US007955395B2

(12) United States Patent
Shea et al.

(10) Patent No.: US 7,955,395 B2
(45) Date of Patent: Jun. 7, 2011

(54) UNIVERSAL LINER

(75) Inventors: Jeffrey J. Shea, Memphis, TN (US); Vincent W. Shotton, Cordova, TN (US); David C. Kelman, Collierville, TN (US)

(73) Assignee: Smith & Nephew, Inc., Memphis, TN (US)

(*) Notice: Subject to any disclaimer, the term of this patent is extended or adjusted under 35 U.S.C. 154(b) by 654 days.

(21) Appl. No.: 11/077,590

(22) Filed: Mar. 11, 2005

(65) Prior Publication Data

US 2005/0240276 A1 Oct. 27, 2005

Related U.S. Application Data

(60) Provisional application No. 60/552,296, filed on Mar. 11, 2004.

(51) Int. Cl.
*A61F 2/34* (2006.01)

(52) U.S. Cl. .................. 623/22.28; 623/22.24

(58) Field of Classification Search ............. 623/22.21, 623/22.24–22.29, 22.11, 22.12, 22.17, 22.19–22.39
See application file for complete search history.

(56) References Cited

U.S. PATENT DOCUMENTS

| | | |
|---|---|---|
| 3,656,184 A | 4/1972 | Chambers |
| 3,894,297 A | 7/1975 | Mittelmeier et al. |
| 4,241,463 A | 12/1980 | Khovaylo |
| 4,279,041 A | 7/1981 | Bucholz |
| 4,619,658 A | 10/1986 | Pappas et al. |
| 4,624,674 A | 11/1986 | Pappas et al. |
| 4,676,798 A | 6/1987 | Noiles |
| 4,678,472 A | 7/1987 | Noiles |
| 4,770,658 A | 9/1988 | Geremakis |
| 4,798,610 A | 1/1989 | Averill et al. |
| 4,908,033 A | 3/1990 | Frey et al. |
| 4,919,674 A | 4/1990 | Schelhas |
| 4,936,855 A | 6/1990 | Sherman |
| 4,950,299 A | 8/1990 | Noiles |
| 4,960,427 A | 10/1990 | Noiles |
| 5,002,577 A | 3/1991 | Bolesky et al. |
| 5,019,105 A | 5/1991 | Wiley |
| 5,049,158 A | 9/1991 | Engelhardt et al. |
| 5,062,853 A | 11/1991 | Forte |
| 5,133,763 A | 7/1992 | Mullers |
| 5,222,984 A | 6/1993 | Forte |
| 5,226,917 A | 7/1993 | Schyver |

(Continued)

FOREIGN PATENT DOCUMENTS

CH  644 511 A  8/1984

(Continued)

OTHER PUBLICATIONS

Translation of FR 2684544.*

(Continued)

*Primary Examiner* — Corrine M McDermott
*Assistant Examiner* — Megan Wolf
(74) *Attorney, Agent, or Firm* — Kilpatrick Townsend & Stockton LLP

(57) ABSTRACT

The present invention relates to universal liner assemblies for use during hip joint replacement surgeries, kits providing a plurality of universal liners, and methods of manufacturing and implanting the universal liners. The universal liners allow the surgeon a greater degree of selection of liners and shells, without being tied to typical liner/shell connections based on material connection constraints.

36 Claims, 7 Drawing Sheets

U.S. PATENT DOCUMENTS

| | | | |
|---|---|---|---|
| 5,263,988 A | 11/1993 | Huebner | |
| 5,310,408 A | 5/1994 | Schryver et al. | |
| 5,314,487 A | 5/1994 | Schryver et al. | |
| 5,314,491 A | 5/1994 | Thongpreda et al. | |
| 5,358,532 A | 10/1994 | Evans et al. | |
| 5,383,938 A | 1/1995 | Rohr et al. | |
| 5,425,778 A | 6/1995 | Zichner et al. | |
| 5,458,649 A | 10/1995 | Spotorno et al. | |
| 5,507,826 A | 4/1996 | Besselink et al. | |
| 5,549,681 A | 8/1996 | Segmuller et al. | |
| 5,549,693 A | 8/1996 | Roux et al. | |
| 5,658,348 A | 8/1997 | Rohr, Jr. | |
| 5,676,704 A | 10/1997 | Ries et al. | |
| 5,725,587 A * | 3/1998 | Garber | 623/22.24 |
| 5,725,591 A | 3/1998 | DeCarlo, Jr. et al. | |
| 5,782,928 A | 7/1998 | Ries et al. | |
| 5,800,555 A | 9/1998 | Gray | |
| 5,824,108 A | 10/1998 | Huebner | |
| 5,879,404 A | 3/1999 | Bateman et al. | |
| 5,916,270 A | 6/1999 | Lipman | |
| 5,931,870 A | 8/1999 | Cuckler et al. | |
| 5,935,175 A | 8/1999 | Ostiguy, Jr. et al. | |
| 5,964,809 A | 10/1999 | Lin et al. | |
| 5,989,293 A | 11/1999 | Cook et al. | |
| 5,989,294 A | 11/1999 | Marlow | |
| 6,042,611 A | 3/2000 | Noiles | |
| 6,042,612 A | 3/2000 | Voydeville | |
| 6,093,208 A | 7/2000 | Tian | |
| 6,096,083 A | 8/2000 | Keller et al. | |
| 6,099,571 A | 8/2000 | Knapp | |
| 6,129,765 A | 10/2000 | Lopez et al. | |
| 6,206,929 B1 | 3/2001 | Ochoa et al. | |
| 6,248,132 B1 | 6/2001 | Harris | |
| 6,328,764 B1 * | 12/2001 | Mady | 623/22.16 |
| 6,475,243 B1 | 11/2002 | Sheldon et al. | |
| 6,488,713 B1 * | 12/2002 | Hershberger | 623/22.11 |
| 6,589,284 B1 * | 7/2003 | Silberer | 623/22.29 |
| 6,916,342 B2 | 7/2005 | Frederick et al. | |
| 7,044,974 B2 * | 5/2006 | Garber et al. | 623/22.21 |
| 7,192,449 B1 * | 3/2007 | McQueen et al. | 623/22.25 |
| 2002/0068980 A1 | 6/2002 | Serbousek et al. | |
| 2002/0147499 A1 * | 10/2002 | Shea et al. | 623/22.21 |
| 2005/0071015 A1 | 3/2005 | Sekel | |
| 2005/0246031 A1 | 11/2005 | Frederick et al. | |
| 2007/0239283 A1 | 10/2007 | Berger et al. | |

FOREIGN PATENT DOCUMENTS

| | | |
|---|---|---|
| DE | 32 15 583 A1 | 12/1982 |
| DE | 93 12 150 U | 10/1993 |
| DE | 199 04 436 A1 | 8/2000 |
| DE | 200 11 728 U | 11/2000 |
| DE | 199 26 923 A | 12/2000 |
| EP | 0 412 438 A | 2/1991 |
| EP | 0 611 008 A | 8/1994 |
| EP | 0 694 294 A1 | 7/1995 |
| EP | 0 694 294 A | 1/1996 |
| EP | 0 773 007 B1 | 5/1997 |
| EP | 0 867 158 A | 9/1998 |
| EP | 0 945 109 A | 9/1999 |
| FR | 2 430 221 A | 2/1980 |
| FR | 2 437 199 A | 4/1980 |
| FR | 2 684 544 | 6/1993 |
| FR | 2 765 100 A | 12/1998 |
| FR | 2 785 524 A | 5/2000 |
| FR | 2 785 525 A | 5/2000 |
| FR | 2 795 302 A | 12/2000 |
| WO | WO 94/05234 | 3/1994 |
| WO | WO 95/22944 | 8/1995 |
| WO | WO 01/76511 A | 10/2001 |
| WO | WO 02/00141 A | 1/2002 |
| WO | WO 02/087476 A1 | 11/2002 |
| WO | WO 2005/087141 | 9/2005 |

OTHER PUBLICATIONS

T. Cobb, et al., The Elevated-Rim Acetabular Liner in Total Hip Arthroplasty: Relationship to Postoperative Dislocation, Journal of Bone and Joint Surgery, vol. 78-A, No. 1, Jan. 1996, pp. 80-86.

CeraNews Special DUOLOX®-System aus BIOLOX® forte, Feb. 1998, four pages.

Anderson, et al. "Constrained Acetabular Components," *The Journal of Arthroplasty*, 9(1):17-23 (1994).

Lombardi, et al., "Preliminary Report on the S-ROM™ Constraining Acetabular Insert: A Retrospective Clinical Experience," *Orthopedics*, 14(3):297-303 (1991).

Brochure entitled "Howmedica Osteonics Constrained Acetabular Insert Surgical Protocol," *Stryker Howmedica Osteoncs*, 11 pages (1999).

Brochure entitled Ringloc® Constrained Liner Technique, *Biomet Inc.*, 6 pages (1998).

Tradonsky, et al., "A comparison of the Disassociation Strength of Modular Acetabular Components," *Clinical Orthopaedics and Related Research*, 296:154-160 (1993).

Rosner, et al., Cup-Liner Conformity of Modular Acetabular Designs, Orthopaedic Research Laboratories, The Mt. Sinai Medical Center, Cleveland, Ohio 44106, six pages (1995).

Goetz, et al., "Salvage of Total Hip Instability with a Constrained Acetabular Component, " *Clinical Orthopaedics and Related Research*, 355:171-181 (1998).

Goetz, et al., "Salvage of a Recurrently Dislocating Total Hip Prosthesis with Use of a Constrained Acetabular Component. A Retropective Analysis of Fifty-Six Cases," *Journal of Bone and Joint Surgery*, 80-A(4):502-509 (1998).

Cameron, H., "Use of a Constrained Acetabular Component in Revision Hip Surgery," *Contemporary Orthop.*, 23(5):481-484 (1991).

Fisher, et al., "Constrained Acetabular Cup Disassembly," *Journal Arthrop.*, 9(3):325-329 (1994).

Kaper, B., P. et al., "Failure of a Constrained Acetabular Prosthesis of a Total Hip Arthroplasty," *Journal of Bone and Joint Surgery*, 80-A(4):561-565 (1998).

Schulte, et al., "The outcome of Charnley total hip arthroplasty with cement after a minimum twenty-year followup. The results of one surgeon," *Journal of Bone and Joint Surgery*, 75-A(7):961-975 (1993).

Turner, "Postoperative Total Hip Prosthetic Femoral Head Dislocations. Incidence, Etiologic Factors, and Management," *Clinical Orthopaedics and Related Research*, 301:196-204 (1994).

Paterno, et al., "The influence of patient related factors and the position of the acetabular component on the rate of dislocation after total hip replacement," *Journal of Bone and Joint Surgery*, 79A(8) (1997).

Ali Khan, et al., "Dislocation Following Total Hip Replacement," *Journal of Bone and Joint Surgery*, 214-218 (1981).

Hedlundh, et al.. "Influence of Surgical Approach on Dislocations After Charnley Hip Arthroplasty," *Journal of Arthroplasty*, 10(5):609-614 (105).

Kristiansen, et al., "Dislocation Following Total Hip Arthroplasty," *Arch. Orthop. Trauma. Surg.*, 103:375-377 (1985).

Morrey, "Difficult Complications After Hip Joint Replacement Dislocation," *Clinical Orthopaedics and Related Research*, 344:179-187 (1997).

Woo, et al., "Dislocations after Total Hip Arthroplasty," *Journal of Bone and Joint Surgery*, 64-A(9):1295-1306 (1982).

Portland Orthopaedics Brochure entitled 'Biomechanical Performance of the Equator +™ Acetabular Cup UHMWPE Liner . . . the freedom of an active lifestyle,' 02 pages (2006).

\* cited by examiner

UNIVERSAL LINER

This application claims priority to U.S. Provisional Patent Application Ser. No. 60/552,296, filed Mar. 11, 2004, the entire contents of which are hereby incorporated by reference.

FIELD OF THE INVENTION

The present invention relates to universal liners that are particularly useful in joint replacement surgeries.

BACKGROUND

Orthopaedic implants are becoming increasingly prevalent as millions of patients have been treated for degenerative diseases and other conditions that affect proper hip, knee, shoulder and other joint function. Surgery to replace a joint that articulates in a socket often involves removing the damaged parts of the relevant joint and replacing them with prosthetic components.

For example, consider the hip. The hip joint is often called a ball-and-socket joint because the spherical head of the thighbone (femur) moves inside the cup-shaped socket (acetabulum) of the pelvis. To duplicate this action, a hip replacement implant typically has a stem, which fits into the femur and provides stability; a ball, which replaces the spherical head of the femur, and a cup, which replaces the worn-out hip socket. The cup typically features an acetabular shell and a liner.

Each component of the implant is typically provided in various sizes in order to accommodate different body sizes and types. In some designs, the stem and ball are one piece; other designs are modular, allowing for additional customization in fit. Typically, for cementless applications, a shell is implanted into the socket and a liner is implanted into the shell. A modular prosthetic stem is then implanted into the patient's intramedullary canal and a head (or ball) is positioned on the stem. The head is also adapted to be positioned in the liner, so that the prosthetic is allowed to articulate in the liner, just as a bone would articulate within a natural socket.

In choosing the joint implant components to use, a surgeon takes into consideration many factors, such as the patient's age, weight, and activity level, as well as relevant factors relating to the implant itself, such as the type of liner to be used (e.g., ceramic, cross lined polyethylene, ultra high molecular weight polyethylene, metal, and so forth) in conjunction with the type of shell (and thus the locking connection featured by the shell) to be used. The liner and shell are typically chosen together because connections between liners and shells are material-specific and design-specific.

For example, ceramic liner to metal shell (and metal liner to metal shell) connections typically use a Morse taper connection, which means that the outer surface of the liner is tapered slightly in order to cooperate with a corresponding taper on the inner surface of the shell. This allows the liner to lock in the shell via a secure connection formed by the tapers.

By contrast, polyethylene liner to metal shell connections typically use a non-Morse taper connection because of the low push-out force resistance of polyethylene. In other words, a Morse taper connection may not secure a polyethylene liner to a metal shell because a tapered polyethylene liner wants to "push" itself out of the shell. Polyethylene liner to metal shell locking connections will vary, but two common examples are axial locking features and rotational locking features.

However, there may be instances in which the surgeon would prefer to select the liner and the shell independently from one another, e.g., a particular shell may have a preferred bone in-growth feature or a certain implantation feature, or a particular liner may have properties that will be advantageous to that particular patient. A surgeon may not want to use the type of liner that is adapted to cooperate with the particular shell chosen and vice versa. One work-around method that has been used by some surgeons is to apply cement to the pre-existing shell to secure a polyethylene liner. However, there is not currently a system available that provides such flexibility.

Additionally, although many advancements have been made to prolong the life of implants, joint implant surgeries may need to be repeated due to the wear experienced by the artificial joint over prolonged periods of time due. Wear debris can be generated from the articulating movement of the components against one another, the components may loosen, ceramic inserts may fail due to fracture, recurrent dislocation may occur, and so forth. During revision surgery, which is a surgery that replaces a current implant with a new one, the surgeon often needs to remove the shell, liner, and implant and replace them with new components.

One of the problems experienced with revision surgeries is that the shell, which may be have integrated into the patient's bone over time, has to be removed because the liner being used does not have connecting features that correspond to those of the current shell and/or because the connecting features of the current shell are going to be damaged during removal of the current liner.

For example, if the surgeon is planning to use a non-tapered liner, but the currently-implanted shell is tapered, there is no way to create a secure connection. For instance, if a surgeon is removing a ceramic liner and chooses to replace it with a polyethylene liner, the surgeon will have to remove the entire shell and replace it with a shell having a different connection mechanism because the polyethylene liner likely will not engage properly via a Morse taper. There is nothing to hold the polyethylene liner in place, particularly because as polyethylene warms up (e.g., due to body temperature), it expands and tends to pop out. As discussed above, one alternative method of securing a non-fitting polyethylene liner in place during revision surgery is to cement the liner to the cup, but that is not optimal.

Another example of why the shell often needs to be removed during revision surgery is because when the surgeon removes the initial liner (the one implanted during the primary surgery), even if the replacement liner has a connection that corresponds with the current shell, there is often a threadform on the inner surface of the shell that is deformed or damaged during removal of the initial liner. Although this threadform may have helped to secure the initial liner, it will no longer be operable to secure the replacement liner due to its deformation. This is particularly a concern if the surgeon wishes to use a ceramic liner during the revision surgery because the deformed threadform may create a raised edge when the initial liner is removed, preventing a new ceramic liner from being properly received by the shell. A ceramic liner being replaced is at risk of either (a) being cracked or fractured on the raised edge of the threadform during replacement or (b) causing a higher risk of fracture during prolonged use from cyclic fatigue against the deformation.

Thus, it would be advantageous to provide a universal liner that can cooperate with a currently-implanted shell to cut down on trauma to the patient due to removal of the shell. (Many shells are provided with a bone in-growth material (such as a porous coating or a biological material) that has encouraged the patient's bone to fuse with the shell. Accordingly, removal of the shell can cause unnecessary trauma to the patient and removal of extra bone, neither of which are optimal.)

It would also be advantageous to provide a universal liner that gives the surgeon more choices of liner to shell connection pre-operatively.

Accordingly, there is a need in the art for a more universal liner connection.

SUMMARY

The present invention comprehends various embodiments of universal liner assemblies which may be employed, among other things, for use during hip joint replacement surgeries. It also comprehends various kits providing a plurality of universal liners, as well as methods of manufacturing and implanting the universal liners. It is beneficial for various implant components used in connection with joint replacement surgeries to be interchangeable, i.e., for liners of various materials to be able to be used with different types of shells. Additionally, because revision surgeries are common, it is particularly beneficial for a surgeon to be able to choose between universal liners of various materials that can be implanted into a currently-implanted shell.

Embodiments of the universal liners described in this document provide a band assembly and a liner component that are assembled together and provided as a one-piece universal liner. One of the benefits of such universal liners is that the band portion interfaces with the inner portion of the shell, taking the specific material of the liner component (and thus the material-specific connection required for it to interface with the shell) out of the equation.

The band portion may have one or more features that cooperate securely within the shell, such as a tapered slope that interfaces with a tapered shell, anti-rotation features on the band that interface with the liner or an inner portion of the shell, or other feature. The concept is that the band of the universal liner cooperates with and secures the universal liner within the inner portion of the shell.

DETAILED DESCRIPTION OF THE DRAWINGS

Figure 1:
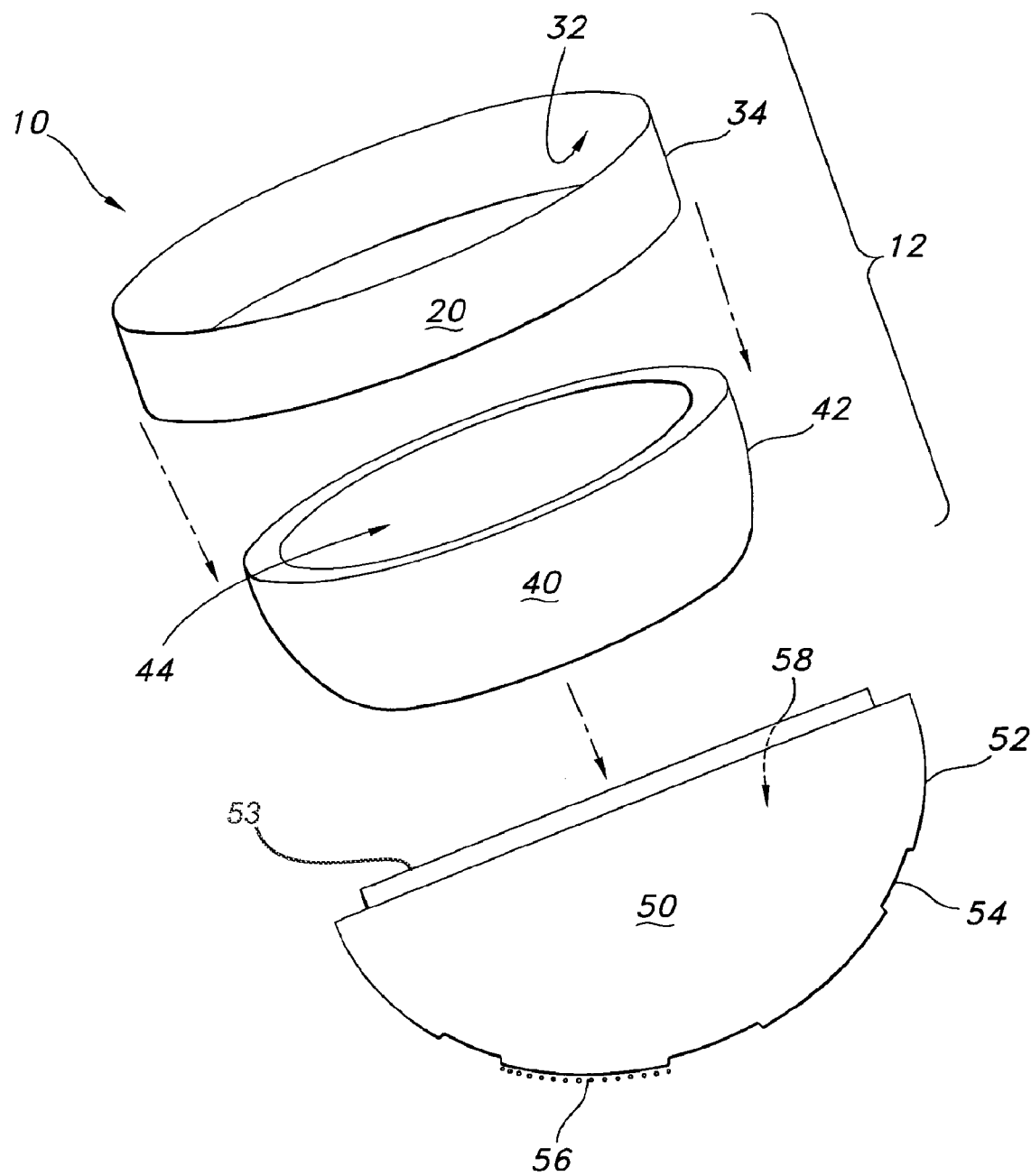
FIG. 1 shows a conceptual exploded perspective view of a universal liner according to certain embodiments of this invention and a side view of a shell adapted to receive the universal liner.

FIG. 1 shows one embodiment of an assembly 10 according to certain aspects of the invention. Referring to FIG. 1, implant assembly 10 features a universal liner 12 that comprises a band 20 and a liner component 40, and a shell 50. During a primary surgery, the outer portion 52 of shell 50 is implanted into a patient's acetabulum, the cup-shaped cavity at the base of the hipbone into which the ball-shaped head of the femur fits. The specific type of shell 50 used is not essential because embodiments of this invention provide a universal liner 12 that can be used in conjunction with any number of shell embodiments 50. For ease of reference, a few features of various shell embodiments will nonetheless be described.

Shell 50 may be made from any biocompatible material that has sufficient strength and wear resistance properties for prolonged use, such as titanium, titanium alloys, cobalt-chromium, surgical steel alloys, or other desired material. It may be press-fit (such that it fits in the prepared socket without cement) or it may be intended to be secured with cement. Shell 50 may have attachment structures 54 that may also receive fasteners used to secure shell 50 in place. Many shells 50 for use with ceramic or metal liners have an inner surface 58 that is slightly tapered, such that it can receive a liner with a corresponding outer tapered surface. Alternatively, shells intended for use with liners of other materials, such as polyethylene, have other locking mechanisms. Shell may have bone in-growth features, such as a porous coating 56 or mesh holes to allow bone to grow into the mesh and essentially "become part of" the bone.

Figure 2:
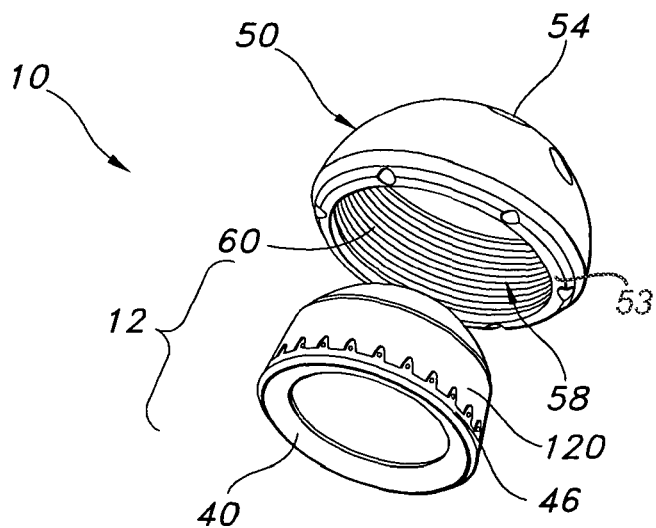
FIG. 2 shows a side perspective view of an assembled universal liner according to certain embodiments of the invention being inserted into a shell.

As shown in FIG. 2, the inner surface 58 of shell 50 is desirably highly polished and mirror-like to reduce wear. See e.g., U.S. Pat. No. 5,310,408, the contents of which are hereby incorporated by this reference. (As discussed further below, the inner surface 32 of the band may also be highly polished.) Even the smallest amount of micro motion of the liner against the shell or the band can create wear particles and debris, which can lead to osteolysis. Providing a highly polished surface on the shell and/or the band can prevent, reduce, or at least slow the generation of debris.

Inner surface 58 may also feature a threadform 60, often a very thin circular or spiral protrusion within shell, which can be used to engage a liner. FIGS. 1 and 2 illustrate shell 50 in the form of a cup having an outer rim 53 that is adapted to receive an assembled universal liner 12.

Embodiments of universal liner 12 have two primary components, band 20 and liner component 40. As shown in at least FIGS. 1-5 and 8-10, the band 20 has a height in a longitudinal direction and a thickness in a radial direction, where the height is greater than the thickness of the band. Band 20 and liner component 40 are manufactured together to provide universal liner 12 to the end-user as a one-piece assembly 12, shown in FIGS. 2, 9 and 10B-C. (These figures show alternate embodiments of bands according to various structures of the invention.)

In use, the outer surface of the band portion interfaces with the inner portion 58 of the shell 50, making the specific material of the liner component 40 (and thus the material-specific connection required for it to interface with the shell) irrelevant. The band is adapted to cooperate with the shell, regardless of the material of the liner component. As described in more detail below, the band portion may have one or more features that cooperate securely within the shell, such as a tapered slope that interfaces with a tapered shell, asperities on the band that interface with an inner portion of the shell, or other feature. The band may also have anti-rotation features that prevent its rotational movement with respect to the shell 50.

As shown in FIG. 1, liner component 40 typically has a shape similar to shell 50, although the diameter of the outer surface 42 of liner component 40 is slightly smaller than the diameter of shell inner surface 58. This allows the liner component 40 to be received by shell 50. Liner component 40 also forms an opening 44 that is adapted to receive the head of an implant (not shown) and allow the head to slide smoothly inside the acetabular implant. The surface of opening 44 may also be highly-polished or smooth to allow the implant head to articulate naturally within liner component 40.

Figure 11:
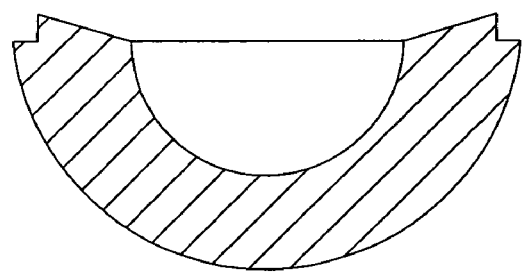
FIGS. 11-12 show alternate liners that may be used with universal liners according to various embodiments of the invention.
Figure 12A:
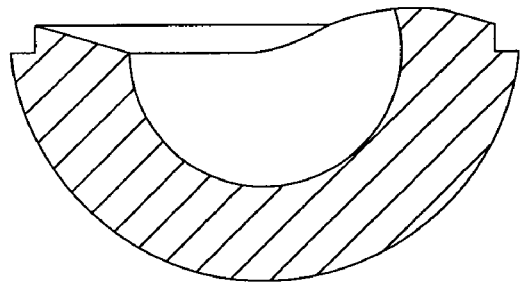
Figure 12B:
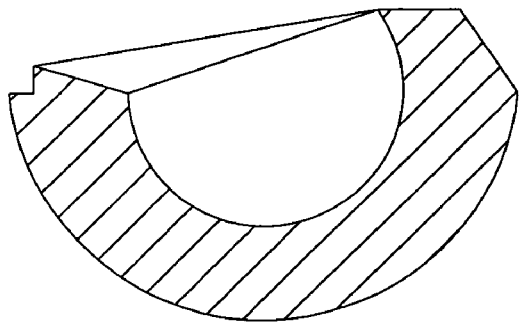

The liners shown in FIG. 1-10 are standard (or 0°) liners. Their opening surface 44 is relatively flush with the shell 50 in use. All embodiments of the invention described herein are also useable with wide chamfer liners (an example of which is shown in FIG. 11), which in some instances, can provide a greater range of motion, and anteversion liners (examples of which are shown in FIGS. 12A and 12B). Other types of liners for use with this invention include overhang and lip liners. In general, any liner that is adapted to cooperate with a shell may be used with various embodiments of this invention.

Liner component 40 may be comprised of any biocompatible material, although common bearing materials include metal, cobalt-chromium, surgical steel, surgical steel alloys, diamond coated metal, ceramic, diamond coated ceramic, polyethylene (e.g., cross linked polyethylene, ultra high molecular weight polyethylene), biocompatible polymers, combinations thereof, or any other type of material having sufficient biocompatibility, strength and wear resistance properties for prolonged use. FIGS. 1 and 2 illustrate how liner outer surface 42 receives band 20 or 120 to form universal liner 12. Band 20 is preferably seated such that it is in non-rotational relation to liner component 40. It has an inner seating surface 32 to cooperate with liner 40 and an outer seating surface 34 to cooperate with shell 50 in use.

The inner seating surface 32 of the band may also have a mirror-like polished surface. In this embodiment, the shiny polished surface faces the liner so that any relative motion between the liner and band will generate minimal liner debris. The polished surface has a roughness of preferably less than eight (8) micro inches.

As shown in FIG. 2, band 20 is assembled integrally around liner component 40. For the purposes of this application, "integral" and "integrally" are used to mean that the band is attached to the liner in such a way that it is not easily removable and so that the universal liner is a one-piece assembly. Band may be formed of any biocompatible material that has sufficient strength and wear resistance properties for prolonged use, such as titanium (including commercially-pure titanium), titanium alloys (including alloys with aluminum), cobalt-chromium, surgical steel, surgical steel alloys, PEEK (Polyetheretherketone), nitinol (a combination of nickel and titanium), other shape memory (or elastic) metals and alloys, combinations thereof, or other desired material. Various embodiments of band 20 are shown in FIG. 3-6. Additionally, although the bands are shown in the Figures as being somewhat symmetrical and round, it is possible for the bands to be any shape that corresponds to the shape of the liner, e.g., oblong, egg-shaped, or any other shape that the liner may take.

Figure 3:
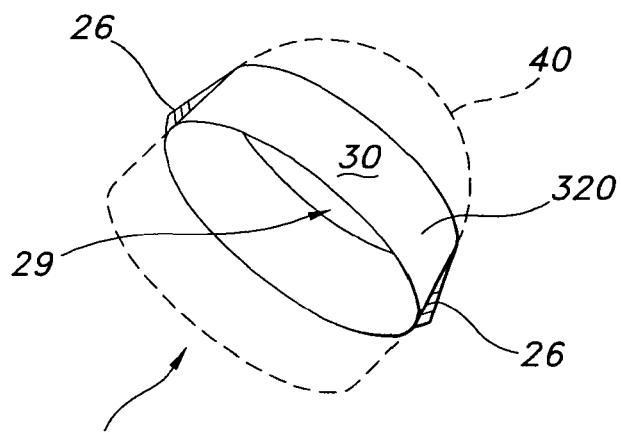
FIG. 3 shows a side perspective view of one embodiment of a band portion of a universal liner according to certain embodiments of the invention.

FIG. 3 shows band 320 with exaggerated taper portions 26 for illustrative purposes only. In this embodiment, band 320 has a first open face 28 and a second open face 29, the faces defining an annular wall 30. Wall 30 provides a sloped or tapered portion 26 of band 320. Taper 26 is provided by wall 30 having a thickness that is greater at first face 28 than at second face 29. The sloped outer surface 26 of band 320 is adapted to mate with the inner surface 58 of shell in Morse taper-fashion, with the taper 26 of wall 30 acting as the male member and the inner surface 58 of the shell 50 acting as the female member to receive universal liner 12. Band 320 is shown in place on a liner component 40, shown in phantom.

Figure 4:
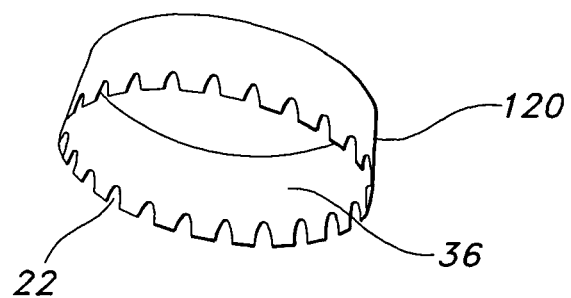
FIG. 4 shows a side perspective view of another embodiment of a band portion of a universal liner according to certain embodiments of the invention having anti-rotation structures.

In certain embodiments, there may be instances when the band 20 would benefit from further rotational stabilization with respect to liner component 40. This is particularly useful with polyethylene liners. During formation of universal liner 12, the band and liner components are manufactured together to provide a one-piece unit 12. If, however, the connection is not rigid enough, there is a chance that band could "spin" or rotate slightly with respect to the liner, preventing a secure connection of universal liner 12 in shell 50. FIG. 4-6 show various embodiments of bands 120 designed to prevent such rotation.

Figure 6A:
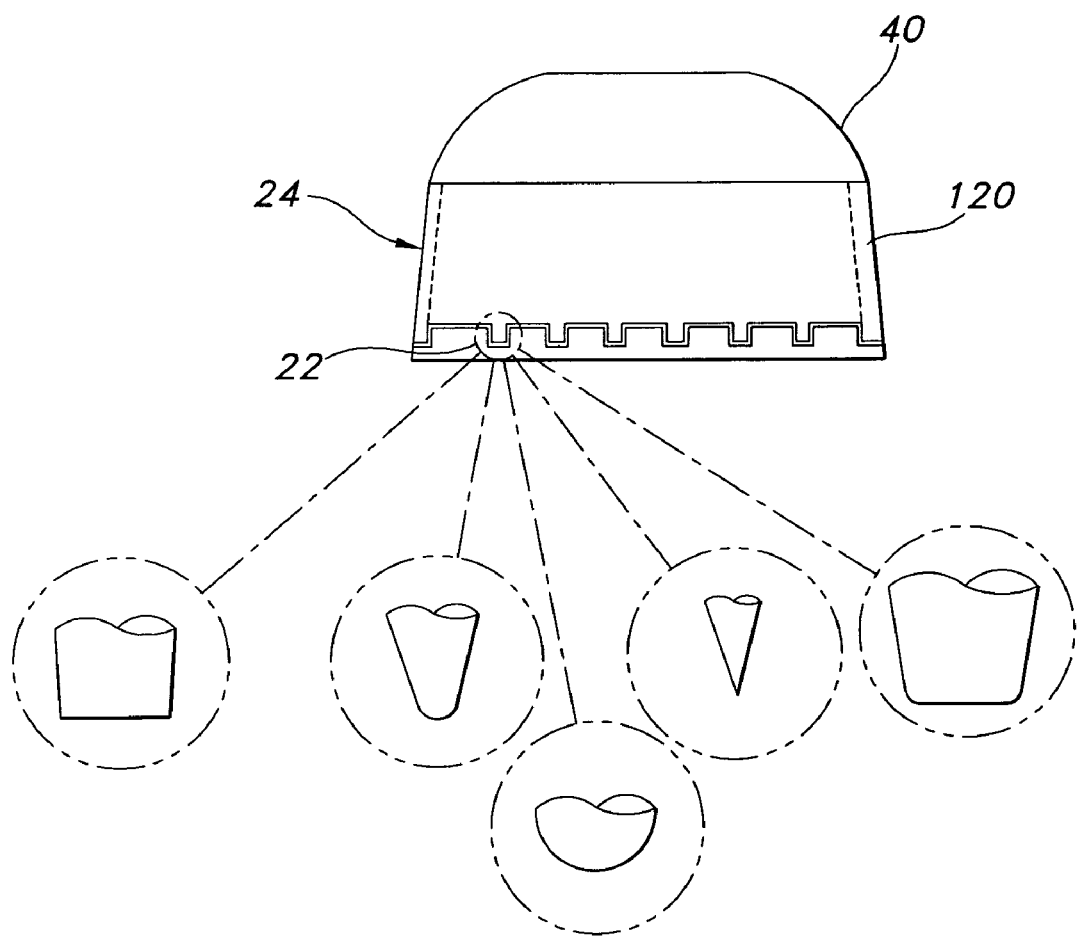
FIG. 6A shows some alternate embodiments for anti-rotation structures.

FIG. 4 shows band 120 having anti-rotation features 22 that are formed in the lower portion 35 of band 120. Anti-rotation features 22 are adapted to cooperate with corresponding structures on liner (described further below) to prevent rotation of band 120 around liner. Anti-rotation features 22 may be manufactured by cutting indented tabs in the lower portion 36 of a band, by providing protrusions on the band, or by any other method that will provide rotational locking between liner and band. In the embodiment shown in FIG. 4, anti-rotation features 22 are V-shaped openings that are adapted to be received by corresponding protrusions on the liner that cooperate with and "catch" anti-rotation features 22. As shown in FIG. 6A, anti-rotation features 22 may be rounded, curved, square, triangular, trapezoidal, cone-shaped, or any other appropriate shape.

Figure 7:
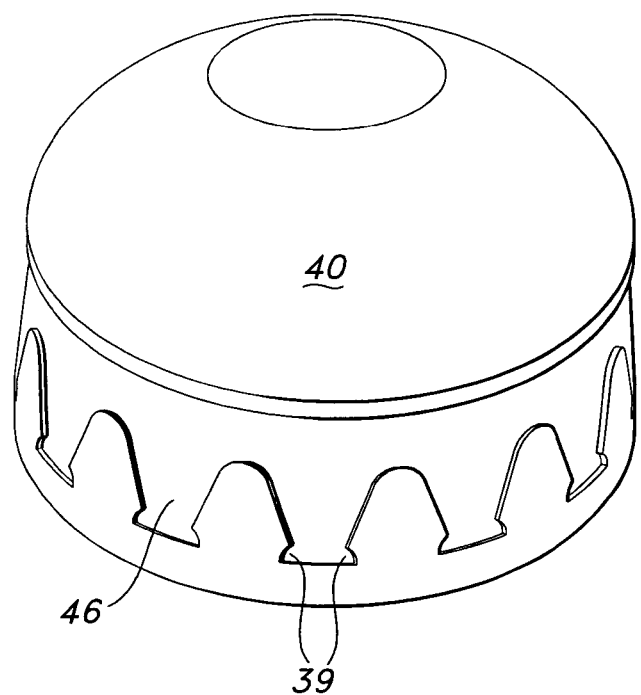
FIG. 7 shows a side view of a liner component adapted to cooperate with a band portion before assembly.

In the embodiment shown in FIG. 4, anti-rotation features 22 cooperate with corresponding features 46 on liner when the two components are formed together. Corresponding features 46 of liner component 40 are shown in FIG. 2 as small protrusions or raised convolutions on liner component 40 at an area where the lower portion 36 of band 120 is seated. Alternate corresponding features 46 are shown in FIG. 7 as indentations that are shaped to receive a similarly-shaped feature on band. The indentations 46 on FIG. 7 form a ledge that is adapted to receive anti-rotation features 22. It is understood that anti-rotation features and corresponding features may be any shape, size, or structure adapted to secure two components together.

Figure 5A:
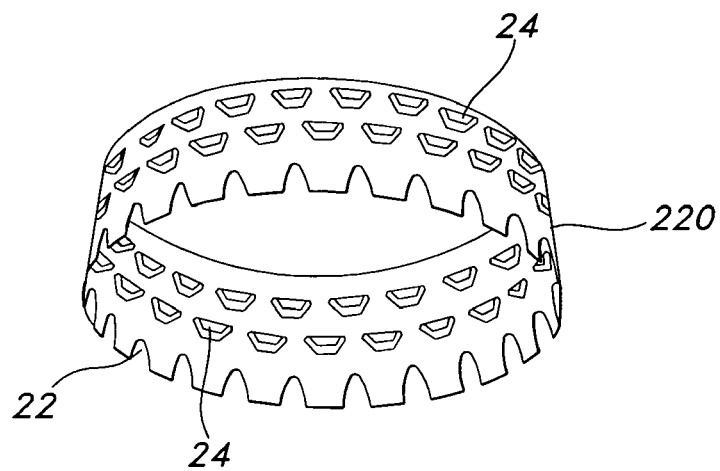
FIGS. 5A-C show side perspective views of further embodiments of band portions of a universal liner according to various embodiments of the invention having anti-rotation structures and asperities.
Figure 5B:
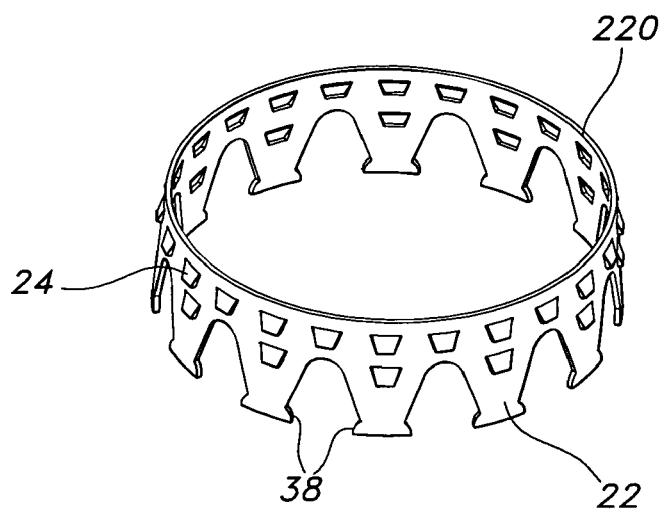
Figure 5C:
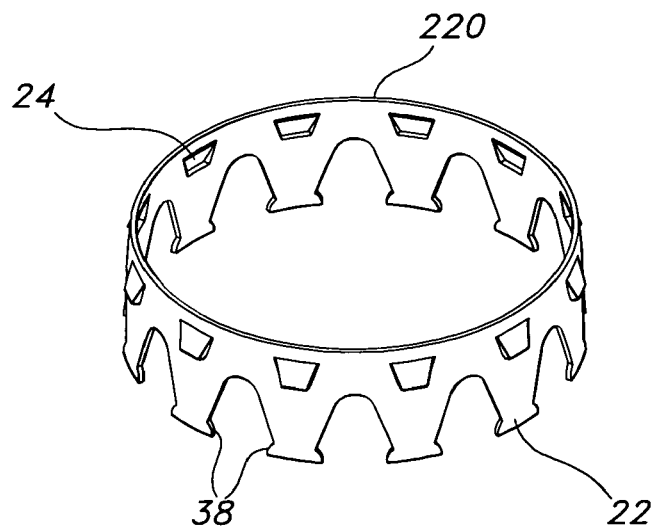

For example, as shown in FIGS. 5B and 5C, anti-rotation features 22 may have catches 38, which act as securing notches. Catches 38 are adapted to cooperate with corresponding receivers 39 on liner 40, as shown in FIG. 7. In this embodiment, when band 120 is positioned over liner 40, catches 38 secure in receiver 39 to prevent liner 120 from rotating around liner 40 in use. Anti-rotation features 22 may alternatively be provided by featuring indentations (or receivers) in the band and providing corresponding protrusions (or catches) on the liner, or by any other appropriate method.

Examples of alternate anti-rotation feature embodiments within the scope of this invention include J-lock features (where either the band or the liner has a protrusion and the other component has a J-shaped groove that engages and locks with the protrusion), keyed slots and corresponding keys, dovetail locking mechanisms, ball and detent mechanisms, and any other features that will prevent one component from rotating with respect to another component. Embodiments of anti-rotation features secure rotation of the liner component 40 with respect to band 20, 120, 220, 320.

FIGS. 5A, 5B, and 5C show band 220 having anti-rotation features 22, as well as axial locking asperities 24. Bands according to various embodiments of this invention may have anti-rotation features 22 alone, axial locking asperities 24 alone, neither, or both of these features. Bands having both of these features are shown and described in FIG. 5A-5C.

FIG. 5A-5C show axial locking asperities 24 as cheese-grater-type teeth. Asperities 24 secure lock universal liner 12 with respect to shell 50. They are adapted to engage the inner surface 58 of the shell 50 in use, such that they flex to allow universal liner 12 to fully lock and secure itself within shell 50.

Asperities 24 can engage threadform 60, which may spiral within inner surface 58 of shell 50. Threadform 60 provides a series of edges for the asperities 24 to "grab" onto. (Note that the threadform may be deformed due to removal of the previous liner in a revision surgery. Although this deformation could present a challenge to liners that are currently available, certain embodiments of the universal liner 12 described herein can use deformed threadform 60 as a securing ledge.) It is understood that asperities 24 may also be mashed inwardly as universal liner 12 is locked within shell 50, causing a resistant securing force.

Asperities 24 can also be used in conjunction with the taper embodiment (shown in phantom on FIG. 6A and described above) to confirm that the taper is locked properly. For example, in order for the taper to be fully locked, it is desirable that there be a bit of space between the outer surface 42 of the liner component 40 and the inner surface 58 of the shell 50; otherwise, there is a chance that the taper 26 is not fully engaged with the tapered sides of the shell. When a band 220 having asperities 24 is used, the small amount of space is taken up by the flexing asperities 24, assuring that the universal liner 12 is axially locked within shell 50.

Figure 6B:
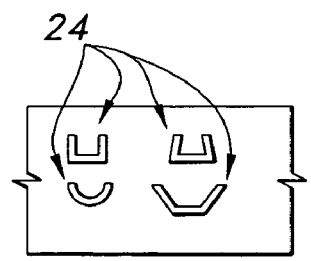
FIG. 6B shows some alternate embodiments for asperities.

Although asperities 24 are shown as cheese-grater-type asperities 24 in FIG. 5, it is understood that asperities may be any type of projection, point, bump, rough surface, hook, or any other feature capable of engaging with inner surface 58 and/or threadform 60 of shell 50. As shown in FIG. 6B, asperities 24 may be provided in any shape (e.g., triangular, square, rounded, or any other appropriate shape), as long as they provide the desired axial locking between band 220 and shell 50. Asperities 24 may be manufactured by cutting or punching out portions of band 120 and allowing them to bend outwardly, by being formed in the band, or by any other appropriate method.

Asperities 24 may be provided in rows (as shown in FIG. 5A-5C) or they may be provided in random spacing order. In the particular embodiment shown in FIG. 5A, there are two rows of asperities 24 extending in a latitudinal direction around the band 220, each having twenty-four asperities 24. FIG. 5B shows a combination of a complete row of asperities 24 extending in a latitudinal direction around the band 220, along with a "broken" row of asperities 24. The "broken" row of asperities 24 forms a row of two asperities 24 arranged in a longitudinal direction along the height of the band 220. FIG. 5C shows one row of larger asperities 24 extending in a latitudinal direction around the band 220. Accordingly, asperities 24 may be provided in any size and in any number, and in rows that extend in either a latitudinal or longitudinal direction around the band. For example, one large asperity could flank the span of band or any number of asperities may be provided in any spacing order on band.

Asperities may also be provided at any angle. The asperities 24 shown in FIG. 5A-5C are angled downward in order to provide axial locking. It is also possible, however, for asperities to be angled further outward (e.g. angled at about 90° from the surface of the band 220) to also provide rotational locking. It is possible to provide a row of downwardly-angled asperities along with a row of outwardly-angled asperities (or upwardly-angled asperities). Another embodiment would be to provide every other asperity at an alternate angle. Any other placement of asperities of various sizes and at alternate angles and orientations are within the scope of this invention.

Figure 8:
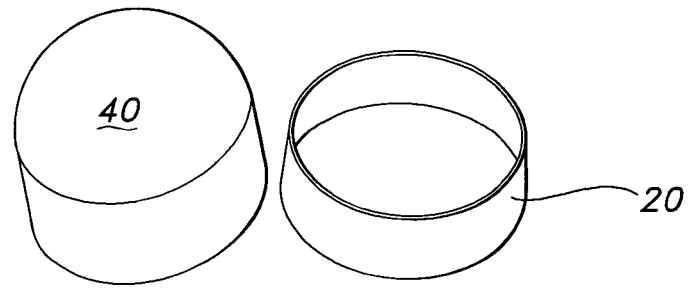
FIG. 8 shows an unassembled band and polyethylene liner component.

FIG. 8 shows one embodiment of band 20 and a polyethylene liner component 40 prior to assembly. Any appropriate method that will secure band 20 to liner component 40 may be used. One manufacturing embodiment that may be used with a polyethylene liner will be referred to as the "shrink-fit method." Polyethylene shrinks when it is cooled, so in the shrink-fit method, the polyethylene liner component 40 is cooled to cause it to shrink to a size that is smaller than its actual size when at room temperature. One possible method of cooling the liner is to immerse it in liquid nitrogen. (Those of ordinary skill in the art will understand that there are many other cooling and manufacturing methods possible.)

Figure 9:
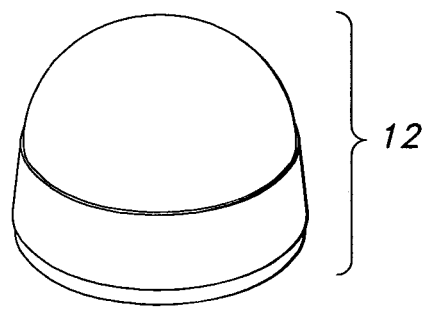
FIG. 9 shows an assembled universal liner according to certain embodiments of the invention.

Once the polyethylene liner component 40 is sufficiently cooled, band 20 (or any of embodiments 120, 220, 320) is fitted over the cooled polyethylene liner component 40 to form universal liner 12, one embodiment of which is shown in FIG. 9. Although the lock is tight at this point, as the polyethylene liner warms, the lock is further enhanced. The lock is often further enhanced when universal liner 12 is implanted due to increased temperature from the patient's body heat, and thus, increased expansion of liner component 40.

Alternatively, band may be a long strip that is applied to the outer surface of liner by any appropriate method, such as welding, sealing, chemical adhesion, laser etching, etc.

Figure 10A:
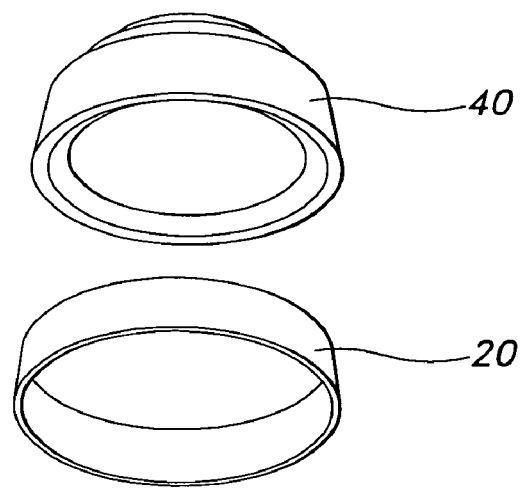
FIG. 10A shows a side perspective view of an alternate embodiment of an unassembled band and ceramic liner component.
Figure 10B:
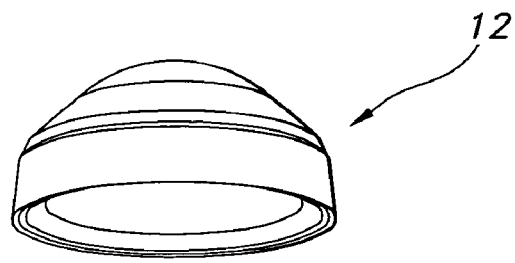
FIG. 10B shows a side perspective view of the components of FIG. 10A in an assembled configuration.

FIG. 10A shows one embodiment of band 20 and a ceramic liner component 40 prior to assembly. Again, any appropriate method that will secure band 20 to liner component 40 may be used. One manufacturing embodiment that may be used with a ceramic liner will be referred to as the "vacuum/pressure method." The ceramic liner component 40 may be subjected to a certain amount of pressure, allowing the band 20 to be fit circumferentially around liner. When pressure is released, the band 20 is integrally seated on liner component 40, as shown in FIG. 10B. Other manufacturing methods include thermal expansion, press fit, or rolling the edges of the band over the circumference of the liner. Additional manufacturing methods would be apparent to those skilled in the art and considered within the scope and spirit of this invention.

Figure 10C:
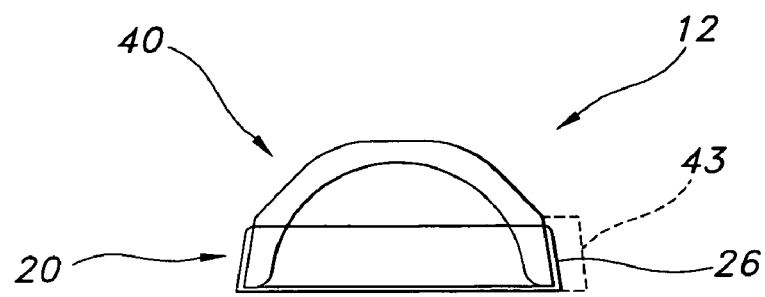
FIG. 10C shows a cut-away view of the assembled configuration of FIG. 10B.

FIG. 10C shows an embodiment of a ceramic universal liner 12 with a ceramic liner component 40 having a tapered side 43. Tapered side 43 features a taper that is shorter than a typical ceramic liner taper, allowing more room inside the metal shell to receive liner, although it is understood that taper may be any desired length. Additionally, band 20 is shown with a tapered surface 26 that does not extend up the entire side 43 of liner 40. This also opens up more room inside the metal shell to receive universal liner 12. (Features that take up less room inside the metal shell allow for the use of larger liners, which allows for the use of larger prosthetic heads, which provides greater range of motion and decreased risk of dislocation.) In the embodiment shown, the interface between the band and the liner accordingly does not take place over the entire outer surface 42 of liner, but instead, is focused on liner side 43. This allows universal liner 12 to cooperate with shell 50 in a secure manner, while also providing more space within shell, allowing the use of a larger liner 12.

The description will now turn to how the universal liner is implanted. During a hip replacement surgery, the surgeon makes an incision over the hip joint. The ligaments and muscles are then separated to allow the surgeon access to the bones of the hip joint. If this is a primary surgery (i.e., not a revision surgery), the femoral head is dislocated from the acetabulum. The natural femoral head is typically removed by cutting through the femoral neck. After the femoral head is removed, cartilage is removed from the acetabulum. The reamer or drill used to remove cartilage may also be used to form the bone in a hemispherical shape to fit the metal shell portion of the acetabular component.

Before implanting the actual shell component, the surgeon will typically use a trial component (a duplicate of the hip prosthesis) to ensure that the intended prosthesis is a good fit. The acetabular shell is then inserted into place using one or more of an impactor, bone screws, or cement.

If the surgeon is conducting a revision surgery, it may be necessary to remove the ball and stem prosthesis and/or remove the liner from the shell. If the surgeon is using a universal liner according to embodiments of the invention, it will not always be necessary to remove the shell from the patient's bone socket because the universal liner is adapted to cooperate with many if not all commercially available shells, regardless of what type of liner it was initially designed for use with.

One particular embodiment of the invention provides a polyethylene-type universal liner that can be installed into an implanted shell that was designed for use with, and originally implanted with, a ceramic liner. Another embodiment provides a ceramic or other non-polyethylene-type universal liner that can be installed into a shell that is currently implanted in a patient.

Once the proper universal liner is chosen, the surgeon will place the universal liner inside the metal shell, typically using an impactor. One of the advantages of this procedure is that the surgeon is able to select the metal shell to be used independently from selecting the universal liner.

To begin replacing the femoral head, rasps are used to shape and hollow out femur to the exact shape of the metal stem of the femoral component. A trial component may be used again to confirm the correct size and shape of the prosthesis chosen. The surgeon will also test the movement of the hip joint.

Once the size and shape of the canal exactly fit the femoral component, the stem is inserted into the femoral canal. If an uncemented femoral stem is to be used, it is held in place by the tightness of the fit into the bone. If a cemented femoral stem is to be used, the femoral canal is rasped to a size slightly larger than the femoral stem. Then epoxy-type cement is used to secure the metal stem to the bone. Finally, the metal ball that replaces the femoral head is attached to the femoral stem. As a final step, the surgeon will typically check the location of the prosthesis with an x-ray or C-arm image.

Changes and modifications, additions and deletions may be made to the structures and methods recited above and shown in the drawings without departing from the scope or spirit of the invention and the following claims.

What is claimed is:

1. A universal liner assembly for use with a shell having an inner surface and an outer rim, comprising:
   (a) a liner component having an outer surface; and
   (b) a band having a continuous annular wall configured to be formed around a portion of the outer surface of the liner component such that, in use, the band is adapted to interface with the inner surface of the shell without extending beyond the outer rim of the shell and to lock the liner component within the shell, regardless of the material of the liner component, the band comprising a plurality of cut out portions defining a plurality of openings extending through the band, wherein the plurality of cut out portions comprise cheese-grater-type asperities.

2. The universal liner assembly of claim 1, wherein a portion of the annular wall of the band comprises a tapered outer seating surface, wherein the inner surface of the shell comprises a tapered inner seating surface, and wherein the tapered outer seating surface of the band is adapted to cooperate with the tapered inner seating surface of the shell.

3. The universal liner assembly of claim 1, wherein the band comprises a plurality of anti-rotation features and the liner component comprises a plurality of corresponding anti-rotation features.

4. The universal liner assembly of claim 3, wherein the anti-rotation features comprise a series of catches and receivers adapted to engage the liner component and band in non-rotational alignment.

5. The universal liner assembly of claim 3, wherein the anti-rotation features comprise (a) a plurality of openings on the band that cooperate with a plurality of protrusions on the liner component, (b) a plurality of protrusions on the band that cooperate with a plurality of indentations on the liner component, or (c) a combination thereof.

6. The universal liner assembly of claim 1, wherein the inner surface of the shell has a threadform and the plurality of cut out portions define axial locking features that engage the threadform to secure the universal liner assembly in place.

7. The universal liner assembly of claim 1, wherein the band has an inner seating surface adapted to cooperate with the outer surface of the liner component, and wherein the inner seating surface of the band is highly polished and adapted to reduce wear.

8. The universal liner assembly of claim 1, wherein the universal liner assembly is adapted for use during a revision surgery and can be received by a shell that is currently implanted in a patient.

9. The universal liner assembly of claim 1, wherein the band comprises titanium, titanium alloys, cobalt-chromium, surgical steel, surgical steel alloys, PEEK (Polyetheretherketone), nitinol, shape memory metals, or any combinations thereof.

10. The universal liner assembly of claim 1, wherein the liner component comprises metal, cobalt-chromium, surgical steel, surgical steel alloys, diamond coated metal, ceramic, diamond coated ceramic, polyethylene, biocompatible polymers, or any combinations thereof.

11. The universal liner assembly of claim 1, wherein the band is dimensioned to retain the liner component in place within the shell.

12. A universal liner assembly for use with a shell having an inner surface comprising:
   (a) a liner component having an outer surface; and
   (b) a band configured to be formed around a portion of the outer surface of the liner component such that, in use, the band is adapted to interface with the inner surface of the shell to lock the liner component within the shell, regardless of the material of the liner component, the band comprising an outer surface and a plurality of cut out portions defining a plurality of openings extending through the band, wherein the plurality of cut out portions comprise cheese-grater-type asperities, and wherein the outer surface of the band comprises a tapered outer seating surface, wherein the inner surface of the shell comprises a tapered inner seating surface, and wherein the tapered outer seating surface of the band is adapted to cooperate with the tapered inner seating surface of the shell, and wherein the band has first and second open faces defined by an annular wall, the annular wall having a first thickness at the first face that is greater than a second thickness at the second face.

13. A universal liner kit, comprising:

a plurality of liner and band assemblies, each assembly comprising a liner component with a band configured to be assembled around a portion of the liner component, wherein, in use, each assembly is dimensioned to receive a spherical implant, wherein the liner components are provided in a plurality of materials selected from the group consisting of metal, cobalt-chromium, surgical steel, surgical steel alloys, diamond coated metal, ceramic, diamond coated ceramic, or any combinations thereof, and wherein the band comprises a plurality of cut out portions defining a plurality of openings extending through the band, and wherein the plurality of cut out portions comprise cheese-grater-type asperities, and wherein the band has first and second open faces defined by an annular wall, the annular wall having a first thickness at the first face that is greater than a second thickness at the second face.

14. The universal liner kit of claim 13, wherein at least one of the bands comprises a sloped outer surface adapted to cooperate with a tapered inner surface of a shell.

15. The universal liner kit of claim 13, wherein at least one of the bands comprises an anti-rotation feature.

16. The universal liner kit of claim 15, wherein the anti-rotation feature comprises (a) openings on the band that cooperate with protrusions on the liner component, (b) protrusions on the band that cooperate with indentations on the liner component, or (c) a combination thereof.

17. The universal liner kit of claim 13, further comprising a set of instruments adapted to place a liner and band assembly within a shell.

18. The universal liner kit of claim 13, further comprising a shell component adapted to receive one of the plurality of liner and band assemblies.

19. The universal liner kit of claim 18, wherein the plurality of cut out portions comprise a plurality of axial locking features that engage the shell to secure the liner and band assembly within the shell.

20. A universal liner assembly, comprising:

(a) a liner component having an outer surface; and (b) a band having (i) a plurality of anti-rotation features adapted to cooperate with the outer surface of the liner component and (ii) a plurality of cut out portions defining a plurality of openings extending through the band, wherein the plurality of cut out portions comprise cheese-grater-type asperities and are adapted to cooperate with a shell to lock the liner component in place, such that, in use, the universal liner assembly is dimensioned to receive a spherical implant and the band is adapted to interface with and secure the liner component in a shell that was initially designed for use with a liner of a different material, wherein the band has first and second open faces defined by an annular wall, the annular wall having a first thickness at the first face that is greater than a second thickness at the second face.

21. The universal liner assembly of claim 20, wherein the universal liner assembly is adapted to cooperate with a shell that was initially designed for use with a ceramic or metal liner, and wherein the shell comprises an inner surface that is tapered.

22. A method of performing a joint revision implant surgery in a patient's hip socket, comprising:

(a) leaving a shell from a previous surgery in place in the patient's hip socket, the shell comprising an inner surface; and (b) placing a universal liner in the shell, the universal liner comprising:

(i) a liner having an outer surface; and (ii) a band configured to be formed around a portion of the outer surface of the liner such that, in use, the band is adapted to interface with the inner surface of the shell and lock the liner within the shell, regardless of the material of the liner, the band having a plurality of cut out portions defining a plurality of openings extending through the band, wherein the plurality of cut out portions comprise cheese-grater-type asperities, and wherein the band has first and second open faces defined by an annular wall, the annular wall having a first thickness at the first face that is greater than a second thickness at the second face.

23. A universal liner assembly for use with a shell having an inner surface, comprising:

(a) a liner component having an outer surface; and (b) a generally cylindrical band having a height in a longitudinal direction and a thickness in a radial direction, wherein the height of the band is greater than the thickness of the band, the band configured to be formed around a portion of the outer surface of the liner component such that, in use, the universal liner assembly is dimensioned to receive a spherical implant and the band is adapted to interface with the inner surface of the shell and lock the liner component within the shell, regardless of the material of the liner component, the band comprising a plurality of cut out portions defining a plurality of openings extending through the band, and wherein the plurality of cut out portions comprise cheese-grater-type asperities.

24. A universal liner assembly comprising:

a shell comprising an inner surface, a plurality of ridges protruding from the inner surface, and an outer rim;

a liner component comprising an outer surface and an apex; and a band comprising a continuous annular wall and a plurality of cut out portions defining a plurality of openings extending through the annular wall, wherein the plurality of cut out portions comprise a plurality of cheese-grater-type asperities, wherein the band is configured to be formed around a portion of the outer surface of the liner component, and wherein the liner component and the band are received within the shell without extending beyond the outer rim of the shell, and the plurality of asperities of the band engage with the plurality of ridges of the shell to thereby lock the liner component within the shell, regardless of the material of the liner component.

25. The universal liner assembly of claim 24, wherein the plurality of asperities on the band are arranged in a plurality of rows positioned around a circumference of the band.

26. The universal liner assembly of claim 25, wherein asperities from a plurality of the rows engage with ridges on the inner surface of the shell.

27. The universal liner assembly of claim 25, wherein the plurality of rows extend in a latitudinal direction around the band.

28. The universal liner assembly of claim 25, wherein the plurality of rows extend in a longitudinal direction on the band.

29. The universal liner assembly of claim 24, wherein the plurality of ridges protruding from the inner surface of the shell comprise a threadform.

30. An assembly comprising:
   (a) a shell having an inner surface and an outer rim; and
   (b) a universal liner comprising:
      (i) a liner component comprising an outer surface; and
      (ii) a band comprising a continuous annular wall that extends around the outer surface of the liner component, and further comprising cut out portions defining a plurality of openings extending through the annular wall, wherein the plurality of cut out portions comprise cheese-grater-type asperities,
   wherein, in use, the universal liner is positioned within the shell so that the band interfaces with the inner surface of the shell to lock the liner component within the shell, regardless of the material of the liner component, and wherein, in use, the universal liner is dimensioned to receive a spherical implant.

31. The universal liner assembly of claim 30, wherein the band is adapted to interface with the inner surface of the shell without extending beyond the outer rim of the shell.

32. The universal liner assembly of claim 30, wherein the shell comprises a plurality of ridges protruding from the inner surface, and wherein at least some of the plurality of asperities of the band engage at least some of the plurality of ridges of the shell to thereby lock the liner component within the shell.

33. The universal liner assembly of claim 32, wherein the plurality of asperities on the band are arranged in a plurality of rows positioned around a circumference of the band.

34. The universal liner assembly of claim 33, wherein asperities from a plurality of the rows engage with ridges on the inner surface of shell.

35. The universal liner assembly of claim 30, wherein, in use, the entirety of the band is positioned between the inner surface of the shell and the outer surface of the liner component.

36. The universal liner assembly of claim 30, wherein the band further comprises a first open face, a second open face, and a plurality of openings that extend through the annular wall of the band from the first open face towards the second open face.

* * * * *